United States Patent
Zhang et al.

(10) Patent No.: US 11,608,741 B2
(45) Date of Patent: Mar. 21, 2023

(54) YIELD ESTIMATION DEVICE AND METHOD FOR LOW-YIELD SHALE GAS RESERVOIR

(71) Applicant: China University of Geosciences (Beijing), Beijing (CN)

(72) Inventors: Yuanfu Zhang, Beijing (CN); Xiaodong Yuan, Beijing (CN); Min Wang, Beijing (CN); Jianguo Zhang, Beijing (CN); Jie Xu, Beijing (CN); Xiangxin Kong, Beijing (CN); Yancui Huo, Beijing (CN)

(73) Assignee: China University of Geosciences (Beijing), Beijing (CN)

( * ) Notice: Subject to any disclaimer, the term of this patent is extended or adjusted under 35 U.S.C. 154(b) by 124 days.

(21) Appl. No.: 17/238,232

(22) Filed: Apr. 23, 2021

(65) Prior Publication Data

US 2021/0239001 A1 Aug. 5, 2021

(30) Foreign Application Priority Data

Dec. 2, 2020 (CN) .......................... 202011403100.0

(51) Int. Cl.
| | |
|---|---|
| *E21B 49/08* | (2006.01) |
| *B01D 19/00* | (2006.01) |
| *E21B 43/34* | (2006.01) |
| *G01N 33/24* | (2006.01) |

(52) U.S. Cl.
CPC ........ *E21B 49/087* (2013.01); *B01D 19/0063* (2013.01); *B01D 19/0068* (2013.01); *E21B 43/34* (2013.01); *G01N 33/241* (2013.01)

(58) Field of Classification Search
CPC ... E21B 43/34; E21B 49/087; B01D 19/0063; B01D 19/0068
See application file for complete search history.

(56) References Cited

U.S. PATENT DOCUMENTS

| | | | | |
|---|---|---|---|---|
| 2,971,376 | A * | 2/1961 | Glasgow | ................. G01F 3/38 96/186 |
| 3,246,757 | A * | 4/1966 | Martin | ................. F16K 31/26 210/124 |
| 5,501,577 | A * | 3/1996 | Cornell | ................. F04B 43/009 417/313 |
| 10,125,557 | B2 * | 11/2018 | Shanks | ................. E21B 21/067 |
| 11,053,669 | B2 * | 7/2021 | Völk | ................. E03B 7/074 |
| 2009/0077936 | A1 * | 3/2009 | Sterner | ................. E21B 49/005 55/385.6 |
| 2012/0253705 | A1 * | 10/2012 | Chen | ................. B01D 17/0208 96/183 |
| 2016/0202709 | A1 * | 7/2016 | Newman, Jr. | ........... G05D 9/12 137/386 |

FOREIGN PATENT DOCUMENTS

| | | | |
|---|---|---|---|
| CN | 104895549 | A * | 9/2015 |
| CN | 109138963 | A * | 1/2019 |
| FI | 73950 | C * | 12/1987 |
| RU | 2355883 | C2 * | 5/2009 |

\* cited by examiner

*Primary Examiner* — John Fitzgerald

(57) ABSTRACT

A yield estimation device for a low-yield shale gas reservoir includes: a separation tank, a pulse gas detector, and a methane concentration detector; wherein a liquid inlet is provided at an upper portion of the separation tank; an exhaust pipe is provided on a top of the separation tank, and the pulse gas detector is installed at a middle section of the exhaust pipe; the methane concentration detector is installed at a tail end of the exhaust; a valve is installed in a liquid outlet; a float is arranged in the separation tank, which is connected to the valve through a telescopic float rod. A yield estimation method includes steps of: inputting flowback fluid into the separation tank through the liquid inlet; discharging the air in the separation tank; performing gas-liquid separation; detecting and displaying the shale gas in real time with the pulse gas detector.

3 Claims, 1 Drawing Sheet

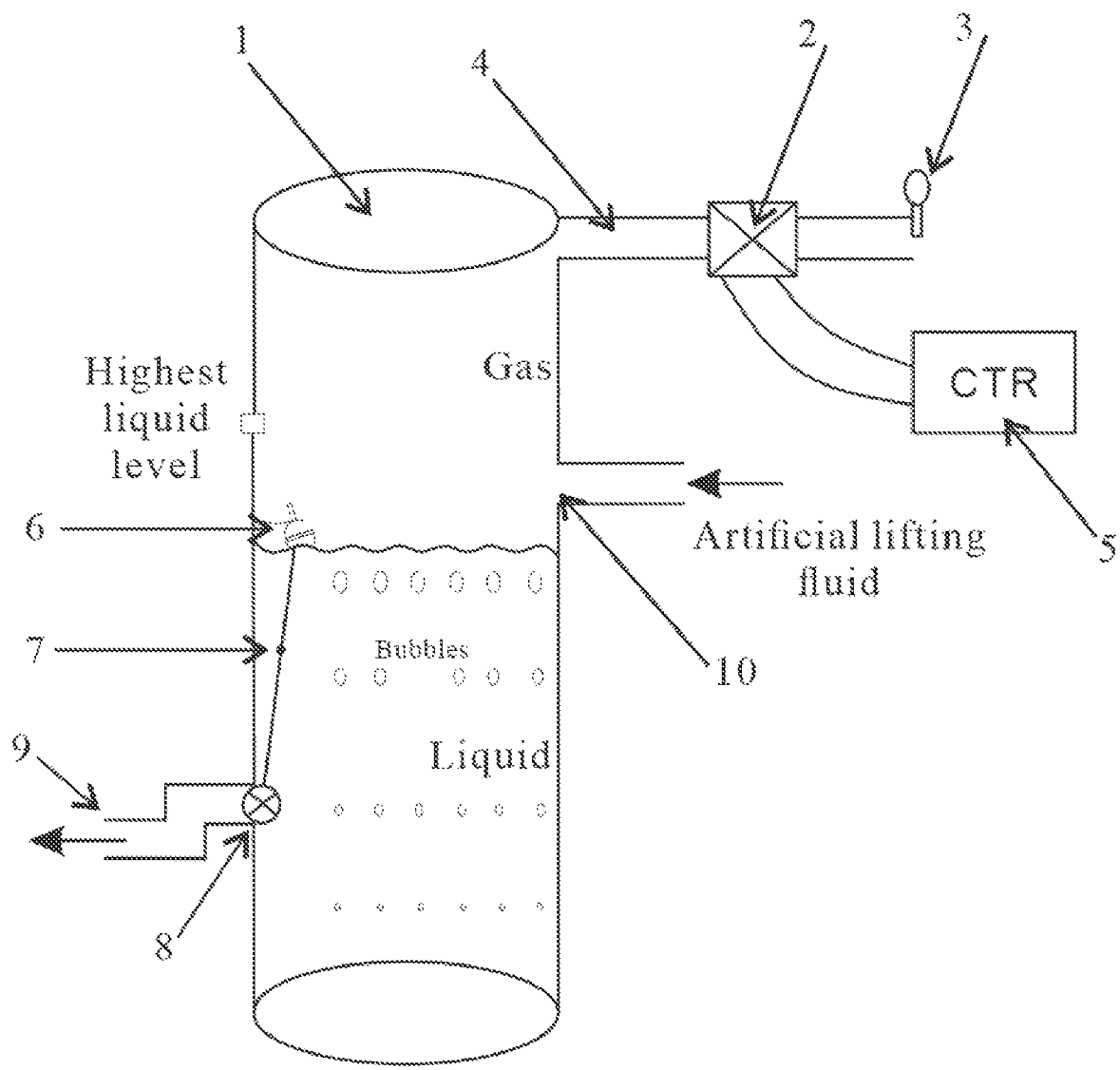

YIELD ESTIMATION DEVICE AND METHOD FOR LOW-YIELD SHALE GAS RESERVOIR

CROSS REFERENCE OF RELATED APPLICATION

The present invention claims priority under 35 U.S.C. 119(a-d) to CN 202011403100.0, filed Dec. 2, 2020.

BACKGROUND OF THE PRESENT INVENTION

Field of Invention

The present invention relates to a technical field of shale gas exploration and development, and more particularly to yield estimation device and method for a low-yield shale gas reservoir.

Description of Related Arts

Since the first shale gas exploration well of China obtained its industrial airflow in 2010, China has achieved leapfrog development in shale gas exploration and development, and it has become the third country in the world to industrialize shale gas production. As of the end of 2015, the cumulative domestic shale gas production of China has exceeded $60*10^8$ m$^3$. However, low and medium-yield wells are the norm for shale gas production in China except for high-yield marine shale gas wells in the Sichuan Basin. Shale gas content and yield are key parameters for shale gas resource evaluation and favorable area optimization, as well as important indexes for evaluating commercial exploitation value. The industrial standard for classifying exploration wells of low-yield shale gas reservoirs is a daily yield of less than $5*10^3$ m$^3$, and the conventional measurement equipment has a minimum sensitivity of 100 m$^3$/d for gas yield. As a result, it is not possible for calculating the yield of shale gas reservoirs which is lower than the sensitivity, and sometimes this can cause problems.

Technical Scheme of Prior Art One

A shale gas analyzer is used to calculate the gas content. In this method, the core taken out on site is directly loaded into the analytical tank, and the core is analyzed by constant temperature or heating with an analytical instrument, and the gas content of the shale gas reservoir in the target interval is estimated by collecting the gas content derived from the core.

Disadvantages of Prior Art One

This method is only used to measure the gas content of cores in coring wells, and the operation is simple, but the core cannot be kept in a sealed state during lifting the core from the wellbore to the earth surface, leading to a certain amount of gas leakage and deviations in the measured data. In addition, this method cannot measure a large number of cores at the same time. Only a certain number of cores are used to estimate the gas content of shale gas reservoirs through analytical gas data collection. Therefore, there is a large error between the calculation result and the actual gas yield of shale gas reservoir. Usually, the calculation result is less than the actual total gas content, and cannot be applied to actual production and mining.

Technical Scheme of Prior Art Two

Casing blowout is used for gas test and yield estimation. This technology uses an extraction pump to separate the flowback fluid through a liquid-gas two-phase separation tank. After the natural gas reaches a certain pressure difference, the gas yield is calculated by a critical pressure gauge. For shale gas reservoirs with low yield, the liquid column difference actually generated in the two-phase separator is used to adjust the size of the orifice plate in the orifice flowmeter, thereby measuring the content of the passing gas.

Disadvantages of Prior Art Two

Although this method can be applied to shale gas test and yield estimation in practice, the accuracy of critical pressure gauge and orifice flowmeter is only 100 m$^3$/d, and the measurement range is narrow. Therefore, it is impossible to accurately measure the shale gas reservoirs with a lower yield. In addition, it is impossible to real-time display the shale gas yield. Only the gas yield over a period of time can be calculated, which has certain limitations.

SUMMARY OF THE PRESENT INVENTION

Aiming at the defects of the prior art, the present invention provides a yield estimation device and method for a low-yield shale gas reservoir, which solves the defects in the prior art.

Accordingly, in order to accomplish the above objects, the present invention provides:

a yield estimation device for a low-yield shale gas reservoir, comprising: a separation tank (1), a pulse gas detector (2), a methane concentration detector (3), and an electronic displayer (5);

wherein the separation tank (1) is cylindrical, and a liquid inlet (10) is provided on a side at an upper portion of the separation tank (1); an exhaust pipe (4) is provided on a top of the separation tank (1) to discharge air in the separation tank (1), and the pulse gas detector (2) is installed at a middle section of the exhaust pipe (4); the methane concentration detector (3) is installed at an exhaust pipe outlet; the pulse gas detector (2) has a gas flow detection ability of 1 m$^3$/d (cubic meter per day); the pulse gas detector (2) is connected to the electronic displayer (5) to display yield data of shale gas in real time; a liquid outlet (9) is provided at a bottom of the separation tank (1), and a valve (8) is installed in the liquid outlet (9) for closing and opening the liquid outlet (9);

a polyethylene float (6) is arranged in the separation tank (1), which is connected to the valve (8) through a telescopic float rod (7); a longest position of the telescopic float rod (7) is at a preset highest liquid level.

The present invention also provides a yield estimation method for the low-yield shale gas reservoir, comprising steps of:

step 1: manually lifting flowback fluid in a wellbore, in such a manner that the flowback fluid enters the separation tank (1) through the liquid inlet (10);

step 2: in an initial state, filling the separation tank (1) with air; after the flowback fluid enters the separation tank (1) through the liquid inlet (10), discharging the air through the exhaust pipe (4) at the top of the separation tank (1); wherein as the flowback fluid enters, the air in the separation tank (1) is discharged; meanwhile, with gas-liquid separation, a natural gas content in the air discharged from the separation tank (1) and the exhaust pipe (4) continues to increase; when the natural gas content detected by the methane concentration detector (3) exceeds 90%, the air in the separation tank (1) is regarded as being fully discharged; then detecting with the pulse gas detector (2);

step 3: carrying shale gas into the separation tank (1) by the flowback fluid to perform gas-liquid separation with water, wherein the water is located at a lower portion of the separation tank (1), and the shale gas resides at the top of the separation tank (1); discharging the shale gas at the top through the exhaust pipe (4), and performing flow statistics when the shale gas passes through the pulse gas detector (2); displaying the yield data of the shale gas in real time;

step 4: keeping the liquid inlet (10) open, in such a manner that the flowback fluid continues to enter the separation tank (1) through the liquid inlet (10), and a liquid level in the separation tank (1) continues to rise; raising the polyethylene float (6) with the liquid level in the separation tank (1); opening the valve (8) in the liquid outlet (9) when the polyethylene float (6) is raised to a longest position of the telescopic float rod (7), which is the preset highest liquid level, thereby discharging the flowback fluid through the liquid outlet (9) after the gas-liquid separation, and ensuring a certain gas volume in the separation tank (1); and step 5: lowering the polyethylene float (6) with the liquid level in the separation tank (1) which continues to drop since the liquid outlet (9) is opened in the step 4; wherein when the liquid level is lower than the preset highest liquid level, the polyethylene float (6) drops with the water level, and the valve (8) blocks the liquid outlet (9) again; then the liquid level in the separation tank (1) rises again; repeating the steps 1-5 to ensure continuity of the gas-liquid separation and shale gas detection in the separation tank (1).

Preferably, the preset highest liquid level is determined according to the gas content in the flowback fluid; a water-soluble gas content in the flowback fluid is measured at any time through experiments to ensure flexible adjustment between the polyethylene float (6), the float rod (7) and the valve (8), thereby ensuring a minimum gas volume in the separation tank (1) is equal to a soluble gas proportion in the flowback fluid.

Compared with the prior art, the present invention has the following advantages:

Detection ability of the shale gas yield is improved to 1 $m^3/d$, which greatly improves the yield estimation accuracy of the low-yield shale gas reservoirs. The present invention provides a novel method and device for gas testing and yield estimation of medium-low-yield shale gas wells which are widely distributed in China.

BRIEF DESCRIPTION OF THE DRAWINGS

FIGURE is a perspective view of a yield estimation device for a low-yield shale gas reservoir according to an embodiment of the present invention.

DETAILED DESCRIPTION OF THE PREFERRED EMBODIMENT

In order to make the objectives, technical solutions, and advantages of the present invention clearer, the present invention will be further described in detail with the accompanying drawing and embodiment.

Referring to the FIGURE, a yield estimation device for a low-yield shale gas reservoir is illustrated, comprising: a separation tank 1, a pulse gas detector 2, a methane concentration detector 3, and an electronic displayer 5.

The separation tank 1 is cylindrical, and a liquid inlet 10 is provided on a side at an upper portion of the separation tank 1; an exhaust pipe 4 is provided on a top of the separation tank 1 to discharge air in the separation tank 1, and the pulse gas detector 2 is installed at a middle section of the exhaust pipe 4; the methane concentration detector 3 is installed at an exhaust pipe outlet.

The pulse gas detector 2 has a gas flow detection ability of 1 $m^3/d$; the pulse gas detector 2 is connected to the electronic displayer 5 to display yield data of shale gas in real time; a liquid outlet 9 is provided at a bottom of the separation tank 1, and a valve 8 is installed in the liquid outlet 9 for closing and opening the liquid outlet 9;

A polyethylene float 6 is arranged in the separation tank 1, which is lighter than water and has good corrosion resistance to raise with the water level in the separation tank 1. The polyethylene float 6 is connected to the valve 8 through a telescopic float rod 7; a longest position of the telescopic float rod 7 is at a preset highest liquid level.

A yield estimation method for the low-yield shale gas reservoir based on the above device comprises steps of:

Step 1: manually lifting flowback fluid in a wellbore, in such a manner that the flowback fluid enters the separation tank 1 through the liquid inlet 10.

Step 2: in an initial state, filling the separation tank 1 with air; after the flowback fluid enters the separation tank 1 through the liquid inlet 10, discharging the air through the exhaust pipe 4 at the top of the separation tank 1; wherein as the flowback fluid enters, the air in the separation tank 1 is discharged; meanwhile, with gas-liquid separation, a natural gas content in the air discharged from the separation tank 1 and the exhaust pipe 4 continues to increase; when the natural gas content detected by the methane concentration detector 3 exceeds 90%, the air in the separation tank 1 is regarded as being fully discharged; then detecting with the pulse gas detector 2.

Step 3: carrying shale gas into the separation tank 1 by the flowback fluid to perform gas-liquid separation with water according to density and solubility, wherein the water is located at a lower portion of the separation tank 1, and the shale gas resides at the top of the separation tank 1; discharging the shale gas at the top through the exhaust pipe 4, and performing flow statistics when the shale gas passes through the pulse gas detector 2; displaying the yield data of the shale gas in real time.

Step 4: keeping the liquid inlet 10 open, in such a manner that the flowback fluid continues to enter the separation tank 1 through the liquid inlet 10, and a liquid level in the separation tank 1 continues to rise; raising the polyethylene float 6 with the liquid level in the separation tank 1 since the polyethylene float 6 is lighter than water and has good corrosion resistance; opening the valve 8 in the liquid outlet 9 when the polyethylene float 6 is raised to a longest position of the telescopic float rod 7, which is the preset highest liquid level, thereby discharging the flowback fluid through the liquid outlet 9 after the gas-liquid separation, and ensuring a certain gas volume in the separation tank 1.

Preferably, the preset highest liquid level is determined according to the gas content in the flowback fluid; a water-soluble gas content in the flowback fluid is measured at any time through experiments to ensure flexible adjustment between the polyethylene float 6, the float rod 7 and the valve 8, thereby ensuring a minimum gas volume in the separation tank 1 is equal to a soluble gas proportion in the flowback fluid.

Step 5: lowering the polyethylene float 6 with the liquid level in the separation tank 1 which continues to drop since the liquid outlet 9 is opened in the step 4; wherein when the liquid level is lower than the preset highest liquid level, the polyethylene float 6 drops with the water level, and the valve 8 blocks the liquid outlet 9 again; then the liquid level in the separation tank 1 rises again; repeating the steps 1-5 to ensure continuity of the gas-liquid separation and shale gas detection in the separation tank 1.

One skilled in the art will understand that the embodiment of the present invention as described above is exemplary only and not intended to be limiting. Those of ordinary skill in the art can make various modifications and combinations without departing from the essence of the present invention based on the technical enlightenment disclosed in the present invention, and these modifications and combinations still fall within the protection scope of the present invention.

What is claimed is:

1. A yield estimation device for a low-yield shale gas reservoir, comprising: a separation tank (1), a pulse gas detector (2), a methane concentration detector (3), and an electronic displayer (5);
    wherein the separation tank (1) is cylindrical, and a liquid inlet (10) is provided on a side at an upper portion of the separation tank (1); an exhaust pipe (4) is provided on a top of the separation tank (1) to discharge air in the separation tank (1), and the pulse gas detector (2) is installed at a middle section of the exhaust pipe (4); the methane concentration detector (3) is installed at an exhaust pipe outlet; the pulse gas detector (2) has a gas flow detection ability of 1 m$^3$/d (cubic meter per day); the pulse gas detector (2) is connected to the electronic displayer (5) to display yield data of shale gas in real time; a liquid outlet (9) is provided at a bottom of the separation tank (1), and a valve (8) is installed in the liquid outlet (9) for closing and opening the liquid outlet (9);
    a polyethylene float (6) is arranged in the separation tank (1), which is connected to the valve (8) through a telescopic float rod (7); a longest position of the telescopic float rod (7) is at a preset highest liquid level.

2. A yield estimation method for the low-yield shale gas reservoir with the yield estimation device as recited in claim 1, comprising steps of:
    step 1: manually lifting flowback fluid in a wellbore, in such a manner that the flowback fluid enters the separation tank (1) through the liquid inlet (10);
    step 2: in an initial state, filling the separation tank (1) with air; after the flowback fluid enters the separation tank (1) through the liquid inlet (10), discharging the air through the exhaust pipe (4) at the top of the separation tank (1); wherein as the flowback fluid enters, the air in the separation tank (1) is discharged; meanwhile, with gas-liquid separation, a natural gas content in the air discharged from the separation tank (1) and the exhaust pipe (4) continues to increase; when the natural gas content detected by the methane concentration detector (3) exceeds 90%, the air in the separation tank (1) is regarded as being fully discharged; then detecting with the pulse gas detector (2);
    step 3: carrying shale gas into the separation tank (1) by the flowback fluid to perform gas-liquid separation with water, wherein the water is located at a lower portion of the separation tank (1), and the shale gas resides at the top of the separation tank (1); discharging the shale gas at the top through the exhaust pipe (4), and performing flow statistics when the shale gas passes through the pulse gas detector (2); displaying the yield data of the shale gas in real time;
    step 4: keeping the liquid inlet (10) open, in such a manner that the flowback fluid continues to enter the separation tank (1) through the liquid inlet (10), and a liquid level in the separation tank (1) continues to rise; raising the polyethylene float (6) with the liquid level in the separation tank (1); opening the valve (8) in the liquid outlet (9) when the polyethylene float (6) is raised to a longest position of the telescopic float rod (7), which is the preset highest liquid level, thereby discharging the flowback fluid through the liquid outlet (9) after the gas-liquid separation, and ensuring a certain gas volume in the separation tank (1); and
    step 5: lowering the polyethylene float (6) with the liquid level in the separation tank (1) which continues to drop since the liquid outlet (9) is opened in the step 4; wherein when the liquid level is lower than the preset highest liquid level, the polyethylene float (6) drops with the water level, and the valve (8) blocks the liquid outlet (9) again; then the liquid level in the separation tank (1) rises again; repeating the steps 1-5 to ensure continuity of the gas-liquid separation and shale gas detection in the separation tank (1).

3. The yield estimation method, as recited in claim 2, wherein the preset highest liquid level is determined according to the gas content in the flowback fluid; a water-soluble gas content in the flowback fluid is measured at any time through experiments to ensure flexible adjustment between the polyethylene float (6), the float rod (7) and the valve (8), thereby ensuring a minimum gas volume in the separation tank (1) is equal to a soluble gas proportion in the flowback fluid.

* * * * *